US009925347B2

(12) United States Patent
Van De Molengraaf et al.

(10) Patent No.: US 9,925,347 B2
(45) Date of Patent: Mar. 27, 2018

(54) CUSHION ELEMENT FOR A PATIENT INTERFACE

(71) Applicant: KONINKLIJKE PHILIPS N.V., Eindhoven (NL)

(72) Inventors: Roland Alexander Van De Molengraaf, Geldrop (NL); Cornelis Petrus Hendriks, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/124,838

(22) PCT Filed: Oct. 1, 2015

(86) PCT No.: PCT/EP2015/072729
§ 371 (c)(1),
(2) Date: Sep. 9, 2016

(87) PCT Pub. No.: WO2016/050929
PCT Pub. Date: Apr. 7, 2016

(65) Prior Publication Data
US 2017/0203069 A1 Jul. 20, 2017

(30) Foreign Application Priority Data

Oct. 2, 2014 (EP) .................................... 14187444

(51) Int. Cl.
*A61M 16/06* (2006.01)
(52) U.S. Cl.
CPC .... *A61M 16/0605* (2014.02); *A61M 16/0633* (2014.02); *A61M 2016/0661* (2013.01); *A61M 2205/0283* (2013.01)

(58) Field of Classification Search
CPC ... A45D 44/22; A47C 31/123; A61L 35/0476; A61L 35/0478; A61L 35/0492;
(Continued)

(56) References Cited

U.S. PATENT DOCUMENTS 6,420,100 B1    7/2002 Trolhan
7,054,680 B1 *  5/2006 Genger ................. A61M 16/00
                                                 128/206.21

(Continued)

FOREIGN PATENT DOCUMENTS

CN    101039641 A    9/2007
CN    201888979 U    7/2011
(Continued)

*Primary Examiner* — Annette Dixon
(74) *Attorney, Agent, or Firm* — Michael W. Haas

(57) ABSTRACT

A patient interface that provides a flow of gas to a user. The interface includes a face-contacting layer and a multi-layer structure covered by the face-contacting layer. The responsive structure includes a plurality of actuators for moving the face-contacting layer. The actuators include a first and second groups of actuators, each of which comprises electrodes arranged in one or more layers. The layers are arranged above each other. The electrodes in the first group of actuators are, with respect to a first axis, transverse to the one or more first and second layers, and are arranged spatially offset relative to the electrodes of the second group actuators such that the electrodes of the first group of actuators do not overlap the electrodes of the second group of actuators.

15 Claims, 2 Drawing Sheets

(58) Field of Classification Search
CPC .............. A61L 35/0496; A61L 35/0878; A61L 35/4818; A61L 35/6803; A61B 5/04085; A61B 5/04087; A61B 5/0476; A61B 5/0478; A61B 5/0492; A61B 5/0496; A61B 5/0878; A61B 5/097; A61B 5/4818; A61B 5/6803; A61B 5/6814; A61H 11/00; A61H 2201/0134; A61H 2201/0196; A61H 2201/0207; A61H 2201/0214; A61H 2201/0228; A61H 2201/0257; A61H 2201/0278; A61H 2201/0292; A61H 2201/1207; A61H 2201/1604; A61H 2201/165; A61H 2205/022; A61H 2205/025; A61H 23/00; A61H 23/0263; A61H 9/0078; A61M 16/00; A61M 16/0003; A61M 16/0051; A61M 16/0057; A61M 16/0066; A61M 16/0069; A61M 16/06; A61M 16/0605; A61M 16/0611; A61M 16/0616; A61M 16/0622; A61M 16/0633; A61M 16/0638; A61M 16/0644; A61M 16/065; A61M 16/0655; A61M 16/0666; A61M 16/0683; A61M 16/0694; A61M 16/08; A61M 16/0808; A61M 16/0816; A61M 16/0825; A61M 16/0841; A61M 16/0858; A61M 16/0875; A61M 16/1095; A61M 16/20; A61M 16/208; A61M 2016/0021; A61M 2016/0027; A61M 2016/0033; A61M 2016/0039; A61M 2016/0661; A61M 2205/02; A61M 2205/0205; A61M 2205/0216; A61M 2205/0222; A61M 2205/0238; A61M 2205/0266; A61M 2205/0283; A61M 2205/0288; A61M 2205/13; A61M 2205/15; A61M 2205/332; A61M 2205/3368; A61M 2205/3375; A61M 2205/3569; A61M 2205/3592; A61M 2205/42; A61M 2205/50; A61M 2205/502; A61M 2205/52; A61M 2205/7527; A61M 2205/7536; A61M 2207/00; A61M 2210/0618; A61M 2230/005; A61M 2230/04; A61M 2230/06; A61M 2230/08; A61M 2230/10; A61M 2230/205; A61M 2230/30; A61M 2230/432; A61M 2230/50; A61M 2230/60; A61M 2230/62; A61M 2230/63; A62B 18/00; A62B 18/025; A62B 18/08; B29C 2045/7343; B29C 33/02; B29C 45/0001; B29C 45/1676; B29C 65/00; B29C 65/02; B29C 65/028; B29C 65/04; B29C 65/48; B29C 66/21; B29C 66/324; B29C 67/246; B29C 69/004; B29K 2075/00; B29K 2083/00; B29K 2105/0061; B29K 2283/00; B29L 2022/025; B29L 2031/4835

USPC ............ 128/200.24, 200.26, 202.22, 204.18, 128/204.21, 204.23, 205.11, 205.12, 128/205.25, 206.14, 206.21, 206.22, 128/206.23, 206.24, 206.25, 206.28, 128/207.12, 848

See application file for complete search history.

(56) References Cited

U.S. PATENT DOCUMENTS

| | | | |
|---|---|---|---|
| 7,204,250 B1* | 4/2007 | Burton | A61B 5/04085 |
| | | | 128/205.23 |
| 8,517,963 B2 | 8/2013 | Larson | |
| 2004/0163648 A1* | 8/2004 | Burton | A61B 5/04085 |
| | | | 128/204.21 |
| 2005/0231677 A1 | 10/2005 | Meredith | |
| 2007/0215161 A1 | 9/2007 | Frater | |
| 2010/0305484 A1 | 12/2010 | Grollier | |
| 2011/0023882 A1 | 2/2011 | Nickol | |
| 2014/0283832 A1* | 9/2014 | Stegman | A61M 16/06 |
| | | | 128/204.21 |

FOREIGN PATENT DOCUMENTS

| | | |
|---|---|---|
| JP | 2011505897 A | 3/2011 |
| WO | WO2009072085 A2 | 6/2009 |
| WO | WO2013067582 A1 | 5/2013 |
| WO | WO2013183018 A1 | 12/2013 |
| WO | WO2013190436 A1 | 12/2013 |
| WO | WO2014024086 A1 | 2/2014 |

* cited by examiner

CUSHION ELEMENT FOR A PATIENT INTERFACE

CROSS-REFERENCE TO RELATED APPLICATIONS

This patent application claims the priority benefit under 35 U.S.C. § 371 of international patent application no. PCT/EP2015/072729, filed Oct. 1, 2015, which claims the benefit of European Patent Application No. EP14187444.6, filed on Oct. 2, 2014. These applications are hereby incorporated by reference herein.

FIELD OF THE INVENTION

The present invention relates to a cushion element for a patient interface for providing a flow of breathable gas to a patient. The present invention particularly relates to a cushion element that is improved with respect to a more efficient prevention of a formation of red marks within the face of the patient. Still further, the present invention relates to a patient interface and a pressure support system which make use of such a cushion element.

BACKGROUND OF THE INVENTION

Patient interfaces, such as masks for covering the mouth and/or nose, are used for delivering gas to a patient. Such gases, like air, cleaned air, oxygen, or any modification of the latter, are submitted to the patient via the patient interface in a pressurized or unpressurized way.

For several chronic disorders and diseases, a long-term attachment of such a patient interface to a patient is necessary or at least advisable.

One non-limiting example for such a disease is obstructive sleep apnea or obstructive sleep apnea syndrome (OSA). OSA is usually caused by an obstruction of the upper airway. It is characterized by repetitive pauses in breathing during sleep and is usually associated with a reduction in blood oxygen saturation. These pauses in breathing, called apneas, typically last 20 to 40 seconds. The obstruction of the upper airway is usually caused by a reduced muscle tonus of the body that occurs during sleep. The human airway is composed of walls of soft tissue which can collapse and thereby obstruct breathing during sleep. Tongue tissue moves towards the back of the throat during sleep and thereby blocks the air passages. OSA is therefore commonly accompanied with snoring.

Different invasive and non-invasive treatments for OSA are known. One of the most powerful non-invasive treatments is the usage of Continuous Positive Airway Pressure (CPAP) or Bi-Positive Airway Pressure (BiPAP) in which a patient interface is connected to a pressure generator via a patient circuit including one or more tubes, wherein the pressure generator blows pressurized gas into the patient interface and into the patient's airway in order to keep it open. Positive air pressure is thus provided to a patient by means of the patient interface that is worn by the patient typically during sleep.

Examples for such patient interfaces are:

nasal masks, which fit over the nose and deliver gas through the nasal passages, oral masks, which fit over the mouth and deliver gas through the mouth, full-face masks, which fit over both the nose and the mouth and deliver gas to both, and nasal pillows, which are regarded as patient interfaces as well within the scope of the present invention and which consist of small nasal inserts that deliver gas directly to the nasal passages.

The patient interface is usually positioned and donned to the patient's head using some kind of headgear. Further, the patient interface may comprise a forehead support. Such a forehead support is often designed as a pad that touches the forehead of a patient during use. It is often included in order to relief the pressure which the patient interface exerts onto the nose bridge.

Wearing a patient interface can be uncomfortable, since for providing an airtight seal between the patient interface and the patient's face, the patient interface has to be worn with a sufficient level of pressure on the face. It is thus evident that users of the patient interfaces experience a lot of disadvantages, wherein the most prominent disadvantage is the formation of facial red marks after a long-term usage of the patient interface. These red marks result from occlusions of blood vessels which arise from the pressure exerted by the patient interface.

A promising concept for preventing uncomfortable pressure points, red marks, indentations, and overall prolonged discomfort is the use of cushion elements that provide an alternating pressure onto the skin of the patient. This restores the skin blood flow in the depressurized part of the cushion element. One approach for providing cushion elements with an alternating pressure distribution is the use of electroactive polymers (EAPs) within the cushion elements. Dielectric elastomer actuators (DEAs) are smart material systems which produce large strains (up to 300%) and belong to the group of EAPs. Based on their simple working principle DEAs transform electric energy directly into mechanical work. DEAs are lightweight and free shapeable.

A DEA is a thin and flexible electroactive polymer sheet enclosed between two compliant electrodes. The thickness of the electroactive polymer sheet is controlled by the applied electrode voltage. Correspondingly, a thickness change results in elongation change. So both the thickness as well as the elongation of the sheet can be controlled. If applied to the skin, the alternating dimensions will impose an alternating pressure or stretch to the skin.

An example for a cushion element that includes EAP-actuators is known from WO 2013/183018 A1. The EAP-actuators used therein continuously alter the skin pressure distribution, provide a slow massaging motion to the skin, and relieve high local pressure peaks.

However, there is still room for improvement. One of the main technical challenges is the technical design and arrangement of such actuators within the cushion element. It is particularly challenging to design and arrange the actuators in such a way that static pressure points may be effectively avoided.

A typical way to produce an EAP actuator is to spin coat or blade the polymer layer and to spray coat or paint the compliant electrode. There is a need to segment the electrodes so that alternating pressure (switching from segment A to segment B) can be realized. However, these electrode-segments are placed at a certain distance away from each other in order to prevent electric arcing from one electrode to the other. The gap between the electrode-segments is usually in the range of 1-2 mm and minimally in the range of 200-500 μm. This gap can be responsible for static pressure points on the cushion element, which can lead to red marks.

SUMMARY OF THE INVENTION

It is an object of the present invention to provide an improved cushion element for a patient interface, wherein the cushion element more effectively overcomes the problem of a red mark formation due to static pressure points on or within the cushion element. It is especially an object of the present invention to provide a cushion including a plurality of electrical actuators for providing an alternating pressure distribution within the cushion element, wherein the technical design and the arrangement of the actuators within the cushion element is improved. An electric arching or short-circuit between the actuators shall be prevented as well.

According to an aspect of the present invention, a cushion element for a patient interface for providing a flow or breathable gas to a patient is presented, wherein the cushion element comprises:

a face-contacting layer for contacting a face of the patient during use of the cushion element; and a multi-layer responsive structure which is covered by the face-contacting layer;

wherein the responsive structure comprises a plurality of actuators for moving the face-contacting layer, wherein said plurality of actuators comprises first actuators belonging to a first group of actuators and second actuators belonging to a second group of actuators, wherein each of the first and the second actuators comprises an electrode, wherein the electrodes of the first actuators are arranged in one or more first layers, and wherein the electrodes of the second actuators are arranged in one or more second layers, wherein the one or more first and second layers are arranged above each other, and wherein the electrodes of the first actuators are, with respect to a first axis transverse to the one or more first and second layers, arranged spatially offset relative to the electrodes of the second actuators such that the electrodes of the first actuators do not overlap the electrodes of the second actuators when being viewed along the first axis.

According to a further aspect of the present invention, a patient interface comprising a cushion element of the above-mentioned type is presented.

According to a still further aspect of the present invention, a pressure support system is presented which comprises a pressure generator for generating a flow of breathable gas, and a patient interface for providing the flow of breathable gas to a patient, wherein the patient interface comprises a cushion element of the above-mentioned type.

Preferred embodiments of the invention are defined in the dependent claims. It shall be understood that the claimed patient interface and the claimed pressure support system have similar and/or identical preferred embodiments as the claimed cushion element and as defined in the dependent claims.

The herein presented cushion element comprises a plurality of actuators which are configured to move the face-contacting layer of the cushion element in a predefined movement pattern in order to prevent a formation of red marks within the face of the patient and to provide a massaging effect. In contrast to prior art cushion elements of this type, the herein presented cushion element provides an improved arrangement of the actuators as well as an improved technical design of the cushion element itself.

The cushion element comprises a face-contacting layer which is configured to contact the face of the patient during use of the cushion element. This face-contacting layer builds the top surface of the cushion element. The face-contacting layer is preferably realized as a continuous layer that (fully) covers a multi-layer responsive structure which is arranged below.

The multi-layer responsive structure itself comprises a plurality of layers which are preferably arranged parallel to one another. It shall be noted that the term "a plurality of" shall mean "at least two".

The responsive structure comprises two groups of layers, a first type of layers, which is herein denoted as first layers, and a second type of layers, which is herein denoted as second layers. It shall be also noted that the terms "first" and "second" are herein only used to distinguish between different parts of the cushion element, but these terms should not imply a specific order or any other special technical meaning. The first and second layers may be of the same technical design. However, these two types of layers are differentiated herein, since the first layers comprise actuators belonging to a first group of actuators (herein denoted as first actuators), whereas the second layers comprise actuators belonging to a second group of actuators (herein denoted as second actuators). Each of the first and the second actuators may also be of the same technical design. However, it is herein differentiated between these two types of actuators, since their arrangement within the responsive structure of the cushion element is different.

Each of the first and second actuators comprises at least one electrode, preferably at least two electrodes. The electrodes of the first actuators are arranged in the first layers of the responsive structures. The electrodes of the second actuators are arranged in the second layers of the responsive structure. The electrodes of the first actuators are not only arranged in layers (first layers) that are different from the layers (second layers) in which the electrodes of the second actuators are arranged. The electrodes of the first actuators are also, with respect to a first axis that is transverse to the first and second layers, arranged spatially offset relative to the electrodes of the second actuators.

The electrodes of the first and second actuators are thus arranged on multiple different layers in an interlaced manner. Such a structure provides several advantages: Electrical arcs and/or short-circuits between the first actuators and the second actuators may be prevented. The first and second layers may nevertheless be arranged very close to one another, such that the gaps between the electrodes may be designed to be relatively small or may even be absent (no gap at all). This guarantees a compact structure and a very efficient actuator arrangement. Even though the layers comprising the electrodes may be packed in a relatively dense manner, the electrodes of the first actuators do not (or at least not significantly) influence the electrodes of the second actuators. Due to the spatially offset arrangement of the electrodes of the first actuators relative to the electrodes of the second actuators with respect to the first axis that is transverse or perpendicular to the first and second layers, the first and second actuators may be actuated in an alternate manner. An alternate actuation of the first and second electrodes causes an undulating or wavelike movement of the face-contacting layer. This undulating or wavelike movement may be, but does not necessarily have to be, a periodic movement. Such a movement of the face-contacting layer prevents static pressure points and provides a smooth massaging effect in the face of the patient.

Each of the first and second actuators is preferably configured to move the face-contacting layer in a direction that is perpendicular to the face-contacting layer, i.e. along the first axis. Upon actuation, the first and second actuators may be configured to either expand or contract the material of the multi-layer responsive structure towards or away from the face of the patient.

It is preferred that the multi-layer responsive structure comprises a plurality of first layers and a plurality of second layers. The first and second layers are preferably arranged on top of each other and parallel to the face-contacting layer. However, the first and second layers do not necessarily need to be parallel to the face-contacting layer, but are nevertheless preferably arranged parallel to one another. It is furthermore preferred that the one or more first layers and the one or more second layers of the multi-layer responsive structure are spaced apart from each other along the first axis. This also means that the electrodes of the first actuators and the electrodes of the second actuators are arranged parallel to each other, wherein they are spaced apart from each other along the first axis. As already mentioned above, the electrodes of the first actuators are arranged spatially offset relative to the electrodes of the second actuators additionally in a direction transverse, or preferably perpendicular thereto.

According to a further preferred embodiment of the present invention, at least one of the one or more first layers is arranged locally in between two second layers. The first and second layers are in other words alternately arranged above each other. The layers are stacked. The top layer of the responsive structure, which is positioned directly below the face-contacting layer, may, for example, be build by a first layer. The next below layer may then be build by a second layer. Again one layer below will be a first layer again, and so on. In this way, each of the first layers (except the ones arranged at the top or bottom of the multi-layer responsive structure) is sandwiched in between two neighboring second layers. Each second layer is then similarly sandwiched between two neighboring first layers.

According to a further embodiment of the present invention, each of the one or more first layers comprises a plurality of spaced apart electrodes of first actuators, and each of the one or more second layers comprises a plurality of spaced apart electrodes of second actuators. It is in this case especially preferred that the electrodes of the first actuators do not overlap the electrodes of the second actuators when being viewed along the first axis, i.e. perpendicular to the first and second layers. It is especially preferred that the electrodes of the first actuators are arranged in a plurality of first columns, and the electrodes of the second actuators are arranged in a plurality of second columns, wherein the first and second columns are parallel to the first axis. The first and second columns are preferably arranged alternately side by side to one another. Each of the first columns preferably comprises a plurality of electrodes of first actuators that are arranged parallel to each other, and each of the second columns comprises a plurality of electrodes of second actuators that are also arranged parallel to each other.

According to an embodiment, each of the first actuators and each of the second actuators further comprise an electroactive polymer material that is integrated in the responsive structure. Said electroactive polymer material is preferably arranged in between the electrodes of the first actuators and in between the electrodes of the second actuators. The electroactive polymer material sandwiched between two electrodes forms an actuator. By the help of such electroactive polymer materials, electric energy may be directly transformed into mechanical work. Electroactive polymers provide the advantage that they are lightweight and free shapeable. By applying an alternating voltage to the electrodes of the first and second actuators, the electroactive polymer material arranged in between them may be forced to expand and contract alternatingly. Due to the arrangement of a plurality of such EAP actuators above each other, the movement of the face-contacting layer is amplified, while it is still possible to use relatively low voltage (low energy). It shall be furthermore noted that some electrodes may belong to two neighboring actuators, whereas electrodes arranged at the borders of the responsive structure may belong to only one actuator.

Examples of such electroactive polymer materials are: piezoelectric polymers, electromechanical polymers, relaxor ferroelectric polymers, electrostrictive polymers, dielectric elastomers, liquid crystal elastomers, conjugated polymers, Ionic Polymer Metal Composites, ionic gels, and polymer gels. However, the present invention is not limited to the use of electroactive polymer materials. Other responsive materials, which could also be used in the actuators according to the present invention, are: electroactive composites, electrostrictive ceramics or crystals, shape memory polymers, photomechanical materials, magnetostrictive materials, chemomechanical materials, and bimetal composites.

According to a further embodiment, each of the electrodes of the first and second actuators has a width (w) of 100 $\mu m \leq w \leq 100$ mm, said width w being measured in a second direction perpendicular to the first direction. Such a width w of the electrodes ensures a large enough but not too large movement of the face-contacting layer.

According to a further embodiment, the electrodes of the first actuators and the electrodes of the second actuators are arranged in concentric loops. Such an arrangement is especially preferred if the cushion element is realized as a nose cushion, a mouth cushion or a nose and mouth cushion. This provides the advantage that even though the face-contacting layer alternatingly moves in the above-mentioned way during use, no pressure leakages occur. However, it shall be noted that such an arrangement is not necessarily needed if the cushion element is realized as a cushion or pad of a forehead support of the patient interface. Such forehead supports usually do not have to form an airtight seal with the patients face.

BRIEF DESCRIPTION OF THE DRAWINGS

These and other aspects of the invention will be apparent from and elucidated with reference to the embodiment described hereinafter. In the following drawings

DETAILED DESCRIPTION OF THE INVENTION

Figure 1:
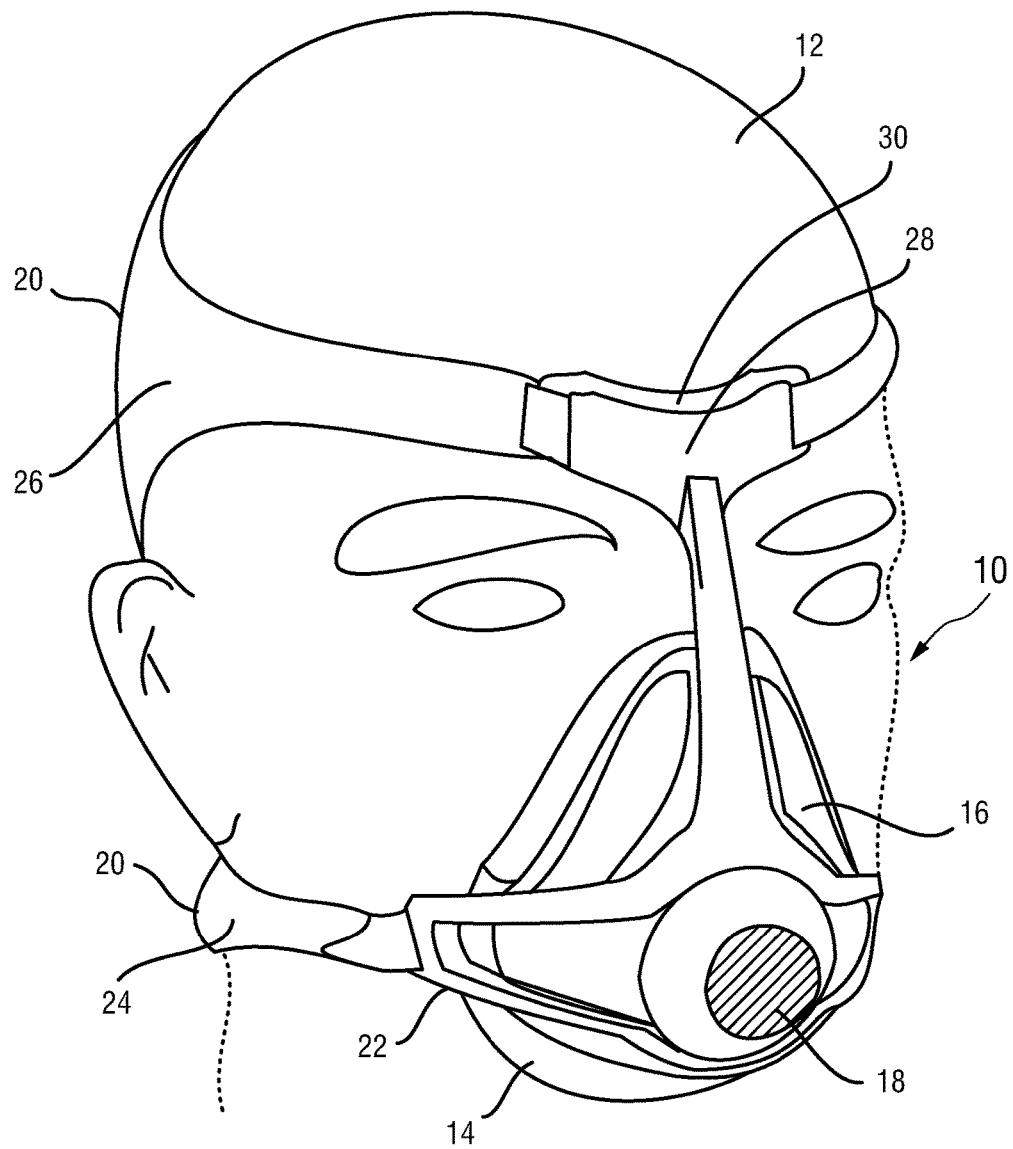
FIG. 1 shows an exemplary embodiment of a patient interface in which a cushion element according to the present invention may be applied.

FIG. 1 shows an exemplary embodiment of a patient interface for delivering a flow of breathable gas to a patient. The patient interface is therein in its entirety denoted by reference numeral 10.

In this embodiment the patient interface 10 is designed as a full-face mask covering the mouth and the nose of a patient 12. It shall be noted that the patient interface 10 may alternatively be designed as a nose mask, a mouth mask or as a total face mask without leaving the scope of the present invention.

The patient interface 10 comprises a cushion element 14 and a mask shell 16. The cushion element 14 is designed to contact the face of the patient 12 and to provide an air-tight seal at the interface between the patient's face and the patient interface 10. The cushion element 14 usually comprises a soft material, like silicon or any other rubber or suitable elastic material. The mask shell 16 provides a flexible, semi-rigid or rigid support structure for holding the cushion element 14. The mask shell 16 is usually connected to the backside of the cushion element 14, wherein the backside is meant to denote the side of the cushion element 14 opposite to the side of the cushion element 14 contacting the patient's face during use. The mask shell 16 may either be releasably or fixedly connected to the cushion element 14. The cushion element 14 and the mask shell 16 thus together form a cavity which is in this case designed to receive the mouth and the nose of the patient 12. It shall be noted that the cushion element 14 and the mask shell 16 may alternatively be formed as one integral piece.

On the opposite side directing away from the patient's face, the mask shell 16 preferably comprises a connector 18. Via this connector 18 the patient interface 10 may be connected to a hose (not shown) via which a pressurized flow of breathable gas can be submitted to the patient interface 10. The mask shell 16 is further connected to a headgear 20. This headgear 20 is used for attaching the patient interface 10 to the patient's head. According to the exemplary embodiment shown in FIG. 1, the headgear 20 comprises a rigid frame 22 and lower and upper headgear straps 24, 26. These lower and upper headgear straps 24, 26 may be connected to the frame 22 of the headgear 20 and used for donning the mask shell 16 and the cushion element 14 to the patient's face.

In the illustrated example the headgear 20 furthermore comprises a forehead support 28. This forehead support 28 allows stabilizing the patient interface 10 while being donned to the patient's face. The forehead support 28 reduces the pressure that is exerted onto the patient's nose during use. In order to make the forehead support 28 as comfortable as possible, the forehead support 28 furthermore comprises a forehead cushion 30 which is attached thereto. This forehead cushion 30 is according to the present invention also considered as a cushion element (similar as cushion element 14).

Figure 2:
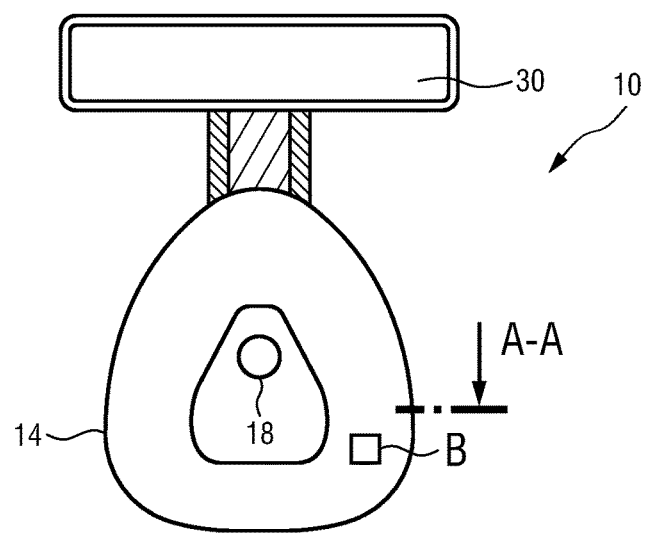
FIG. 2 shows a backside of the patient interface shown in FIG. 1.

FIG. 2 shows a schematic view of the patient interface 10, the cushion element 14 and the forehead support 28 from the other side, i.e. from the side with which the cushion element 14 and the forehead cushion 30 contact the patient's face.

Figure 3A:
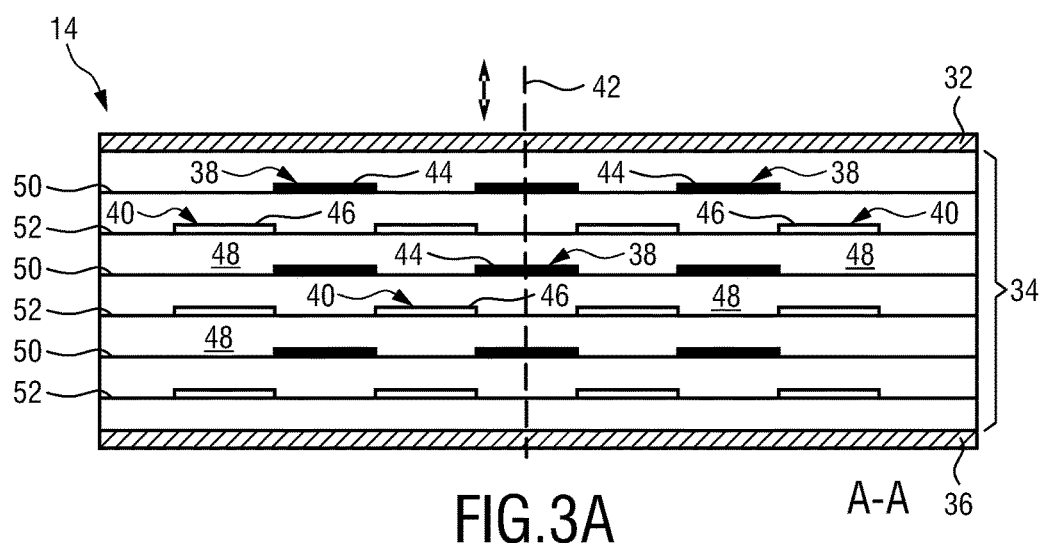
FIG. 3A shows a schematic cross section of an embodiment of the cushion element according to the present invention.
Figure 3B:
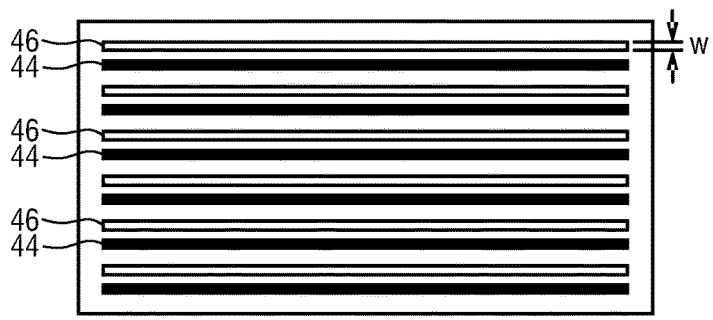
FIG. 3B shows a schematic top view of the embodiment of the cushion element shown in FIG. 3A.

FIGS. 3A and 3B show a schematic cross-sectional view and a schematic top view of the cushion element 14 according to an embodiment of the present invention. The structure and technical design of the cushion element 14 is therein illustrated in detail.

In the illustrated example the cushion element 14 basically comprises three main layers: a face-contacting layer 32, a multi-layer responsive structure 34 and a support layer 36. The face-contacting layer 32 forms the top surface of the cushion element 14 that contacts the patient's face during use. It may be made of a thin elastomeric film and has the function to provide a skin-friendly interface. The support layer 36 is arranged at the backside of the cushion element 14, which backside is usually connected to the mask shell 16. This support layer 36 is preferably made of a rubber material that is stiffer and less resilient than the materials from which the face-contacting layer 32 and the multi-layer responsive layer 34 are made. The face-contacting layer 32 and the multi-layer responsive layer 34 may either comprise the same base material or be made of different materials. The support layer 36 shall provide mechanical stability. However, it shall be noted that this support layer 36 is not necessarily needed if the function of providing mechanical stability is fulfilled by the mask shell 16 itself. The multi-layer responsive layer 34 would in this case be sandwiched between the face-contacting layer 32 and the mask shell 16 instead of being sandwiched between the face-contacting layer 32 and the support layer 36 (as shown in FIG. 3A). Both alternatives are possible. It is also possible that the face-contacting layer 32 forms part of the multi-layer responsive structure 34, i.e. that the face-contacting layer 32 is an integral part of the multi-layer responsive structure 34 and builds its top surface.

One of the central features of the present cushion element 14 is the structure and technical design of the multi-layer responsive structure 34. The multi-layer responsive structure 34 comprises a plurality of actuators 38, 40. These actuators 38, 40 are configured to move the face-contacting layer 32 of the cushion element 14 along a first axis 42 towards and away from the face of the patient 12. The actuators 38, 40 are preferably configured to move the face-contacting layer 32 in a direction that is perpendicular to the face-contacting layer 32, i.e. in a direction that is perpendicular to the interface between the cushion element 14 and the face of the patient 12.

The multi-layer responsive structure 34 comprises two groups of actuators, a first group of actuators comprising the first actuators 38 and a second group of actuators comprising the second actuators 40. Each of the first actuators 38 comprises two opposing electrodes 44, and each of the second actuators 40 comprises two opposing electrodes 46. Each of the first and second actuators 38, 40 further comprise an electroactive polymer material 48 which is arranged in between the electrodes 44 and 46, respectively. The first and second actuators 38, 40 preferably have the same design. However, they differ from each other with respect to their arrangement within the multi-layer responsive structure 34.

The multi-layer responsive structure 34 is internally divided into a plurality of layers. It comprises first layers 50 and second layers 52. These first and second layers 50, 52 are preferably arranged parallel to one another and parallel to the face-contacting layer 32, i.e. preferably perpendicular to the first axis 42. The first layers 50 comprise the electrodes 44 of the first group of actuators 38. The second layers 52 comprise the electrodes 46 of the second group of actuators 40. Each of the first layers 50 comprises a plurality of electrodes 44 of the first actuators 38. Each of the second layers 52 preferably comprises a plurality of electrodes 46 of the second actuators 40. The electrodes 44, 46 are in each layer 50, 52 preferably spaced apart from one another. The first and second layers 50, 52 are arranged on top of each other. It is especially preferred that the first and second layers 50, 52 are alternately arranged on top of each other. This means that each of the first layers 50 (except the first layer 50 arranged at the top of the multi-layer responsive structure 34) is arranged locally in between two neighboring second layers 52. Similarly, each second layer 52 (except the second layer 50 arranged at the bottom of the multi-layer responsive structure 34) is arranged locally in between two first layers 50.

Due to the structure described above, the electrodes 44 of the first actuators 38 are spaced apart from the electrodes 46 of the second actuators 40 along the first axis 42. However, the electrodes 44 of the first actuators 38 are not only spaced apart from the electrodes 46 of the actuators 40 in this direction, but also in a direction transverse thereto. As it can be seen in FIG. 3A, the electrodes 44 of the first actuators 38 are also with respect to the first axis 42 arranged spatially offset relative to the electrodes 46 of the second actuators 40. The electrodes 44 of the first actuators 38 and the electrodes 46 of the second actuators 40 are thus arranged in an interlaced manner, wherein the electrodes 44 are spatially offset from the electrodes 46 in two directions being transverse to each other.

The multi-layer responsive structure 34 thus comprises a plurality of columns which are arranged parallel to one another and perpendicular to the first and second layers 50, 52. The first columns comprise the electrodes 44 of the first actuators 38, and the second columns comprise the electrodes 46 of the second actuators 40. These first and second columns are arranged alternately side by side to one another. In the example illustrated in FIG. 3A, each of the first columns comprises three electrodes of the first actuators 38, and each of the second columns comprises three electrodes 46 of the second actuators 40. One could also say that the first columns and the second columns are spatially offset from one another along the first axis 42. It shall be noted that the first columns may be arranged directly adjacent to the second columns (no gaps in between). This leads to the densest possible arrangement. However, it is also possible that (small) gaps occur in between the first and second columns.

The above-mentioned actuator arrangement within the cushion element 14 provides several advantages:

1. The use of electroactive polymer (EAP) actuators allows producing large strains within the cushion element 14 by applying a voltage to the electrodes 44, 46 of the EAP actuators. The thickness of the EAP layer that is sandwiched in between the electrodes 44, 46, respectively, may be controlled by the applied electrode voltage. Correspondingly, a thickness change in one direction results in an elongation change in the perpendicular direction. So both the thickness as well as the elongation of the cushion element 14 can be controlled. By activating and deactivating the EAP actuators 38, 40, it is thus possible to expand and contract the multi-layer responsive structure 34 in order to move the face-contacting layer 32 along the first axis 42 in a predefined pattern.

2. The first and second EAP actuators 38, 40 are preferably actuated in an alternate manner. This results in an undulating or wavelike movement of the face-contacting layer 32. Such an undulating or wavelike movement of the face-contacting layer 32 preserves the sealing behavior of the cushion element 14 and at the same time provides a smooth massaging effect in the face of the patient 12. Due to the spaced-apart arrangement of the first and second EAP actuators 38, 40 and their alternate activation, it is furthermore possible to prevent static pressure points within the face of the patient 12.

3. Due to the above-mentioned interlaced arrangement of the first and second EAP actuators 38, 40, it is furthermore possible to arrange them very close together. Almost no gaps are necessary between the first actuator columns and the second actuator columns. It is especially preferred that the electrodes 44 of the first actuators 38 do not overlap the electrodes 46 of the second actuators 40 when looking at the cushion element 14 from above or below along the first axis 42. A very compact actuator arrangement may therefore be achieved.

4. Due to the interlaced arrangement of the EAP actuators 38, 40 on different layers 50, 52, short-circuits and electric arching is prevented as well, even though the actuators 38, 40 are arranged relatively close together. Voltages applied to the electrodes 44 of the first actuators 38 do not or at least not strongly influence the electrodes 46 of the second actuators 40.

FIG. 3B shows detail B of the cushion element 14 in a top view. It may be seen that each of the electrodes 44, 46 are preferably realized as elongated stripes which proceed within the multi-layer responsive structure 34 parallel to the face-contacting layer 32, i.e. preferably perpendicular to the first axis 42. In order to provide a sufficient airtight sealing, it is furthermore preferred that these electrode 44, 46 are arranged in concentric closed loops which circumference the mouth and/or nose of the patient 12 during use.

The width w of the electrodes 44, 46 may be designed in a relatively free manner. Experiments of the applicant have, however, shown that the best massaging effects may be achieved if the width w ranges between 100 μm and 100 mm.

It shall be furthermore noted that the above-mentioned structure of the cushion element 14 may not only be used in the main cushion forming the airtight seal of the mask 10, but could be alternatively or additionally also be used in the forehead cushion 30.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A cushion element for a patient interface for providing a flow of breathable gas to a patient, wherein the cushion element comprises:
   a face-contacting layer for contacting a face of the patient during use of the cushion element; and
   a multi-layer responsive structure which is covered by the face-contacting layer;
   wherein the responsive structure comprises a plurality of actuators for moving the face-contacting layer, wherein said plurality of actuators comprises first actuators belonging to a first group of actuators and second actuators belonging to a second group of actuators,
   wherein each of the first and the second actuators comprises an electrode,
   wherein the electrodes of the first actuators are arranged in one or more first layers, and wherein the electrodes of the second actuators are arranged in one or more second layers, wherein the one or more first and second layers are arranged above each other, and
   wherein the electrodes of the first actuators are, with respect to a first axis which is transverse to the one or more first and second layers, arranged spatially offset relative to the electrodes of the second actuators and wherein the electrodes of the first actuators do not overlap the electrodes of the second actuators when being viewed along the first axis.

2. The cushion element according to claim 1, wherein the multi-layer responsive structure comprises a plurality of first layers and a plurality of second layers.

3. The cushion element according to claim 1, wherein the one or more first layers and the one or more second layers of the multi-layer responsive structure are spaced apart from each other along the first axis.

4. The cushion element according to claim 1, wherein the one or more first layers and the one or more second layers of the multi-layer responsive structure are arranged parallel to the face-contacting layer.

5. The cushion element according to claim 1, wherein at least one of the one or more first layers is arranged between two second layers.

6. The cushion element according to claim 1, wherein each of the one or more first layers comprises a plurality of spaced apart electrodes of first actuators, and wherein each of the one or more second layers comprises a plurality of spaced apart electrodes of second actuators.

7. The cushion element according to claim 1, wherein the electrodes of the first actuators are arranged in a plurality of first columns, and the electrodes of the second actuators are arranged in a plurality of second columns, wherein the first and second columns are parallel to the first axis, wherein each of the first columns comprises a plurality of electrodes of first actuators that are arranged parallel to each other and perpendicular to the first axis, and each of the second columns comprises a plurality of electrodes of second actuators that are also arranged parallel to each other and perpendicular to the first axis, and wherein the first and second columns are preferably arranged alternately side by side to one another.

8. The cushion element according to claim 1, wherein each of the first actuators and each of the second actuators further comprises an electroactive polymer material that is integrated in the responsive structure.

9. The cushion element according to claim 8, wherein the electroactive polymer material is arranged between the electrodes of the first actuators and between the electrodes of the second actuators, respectively.

10. The cushion element according to claim 1, wherein the electrodes of the first actuators and the electrodes of the second actuators are arranged in concentric closed loops.

11. The cushion element according to claim 1, wherein each of the electrodes of the first and second actuators has a width of 100 $\mu m \leq w \leq 100$ mm, said width being measured in a second direction transverse to the first axis.

12. The cushion element according to claim 1, wherein the cushion element is one of a nose cushion, a mouth cushion and a forehead cushion.

13. A patient interface for providing a flow of breathable gas to a patient, wherein the patient interface comprises a cushion element according to claim 1.

14. The patient interface according to claim 13, further comprising a voltage source which is connected to the first and second actuators, a control unit that is configured to alternately activate the first and the second actuators by means of the voltage source.

15. A pressure support system, comprising:
a pressure generator for generating a flow of breathable gas; and
a patient interface for providing a flow of breathable gas to a patient, wherein the patient interface comprises a cushion element, wherein the cushion element comprises:
a face-contacting layer for contacting a face of the patient during use of the cushion element; and
a multi-layer responsive structure which is covered by the face-contacting layer;
wherein the responsive structure comprises a plurality of actuators for moving the face-contacting layer, wherein said plurality of actuators comprises first actuators belonging to a first group of actuators and second actuators belonging to a second group of actuators,
wherein each of the first and the second actuators comprises an electrode,
wherein the electrodes of the first actuators are arranged in one or more first layers, and wherein the electrodes of the second actuators are arranged in one or more second layers, wherein the one or more first and second layers are arranged above each other,
wherein the electrodes of the first actuators are, with respect to a first axis which is transverse to the one or more first and second layers, arranged spatially offset relative to the electrodes of the second actuators, and
wherein the electrodes of the first actuators do not overlap the electrodes of the second actuators when being viewed along the first axis.

* * * * *